United States Patent [19]

Yamahira et al.

[11] Patent Number: 4,774,091
[45] Date of Patent: Sep. 27, 1988

[54] LONG-TERM SUSTAINED-RELEASE PREPARATION

[75] Inventors: Yoshiya Yamahira, Kobe; Keiji Fujioka, Amagasaki; Shiegeji Sato, Ibaraki; Yoshihiro Takada, Takatsuki, all of Japan

[73] Assignee: Sumitomo Pharmaceuticals Company, Ltd., Osaka, Japan

[21] Appl. No.: 846,193

[22] Filed: Mar. 31, 1986

Related U.S. Application Data

[63] Continuation-in-part of Ser. No. 660,052, Oct. 12, 1984, abandoned.

[30] Foreign Application Priority Data

Oct. 14, 1983 [JP] Japan ................................ 58-193064
Nov. 1, 1983 [JP] Japan ................................ 58-206226
Dec. 14, 1983 [JP] Japan ................................ 58-236994
Dec. 14, 1983 [JP] Japan ................................ 58-236995
Dec. 14, 1983 [JP] Japan ................................ 58-236996
Apr. 11, 1985 [JP] Japan ................................ 60-77250

[51] Int. Cl.⁴ ............................................. A61K 37/24
[52] U.S. Cl. ...................................... 424/426; 604/60; 424/422; 424/457; 424/458; 424/85.1; 424/85.2; 424/85.4; 514/965; 514/944; 514/774; 514/801; 514/953
[58] Field of Search ...................... 424/36, 37, 22, 422, 424/426; 514/774, 801, 953, 965

[56] References Cited

U.S. PATENT DOCUMENTS

| 106,773 | 8/1870 | Blake ................................ 424/422 |
| 2,498,374 | 2/1950 | Martin ................................ 514/9 |
| 2,518,510 | 8/1947 | Welch . | |
| 2,961,374 | 11/1960 | Lieb et al. ................................ 424/19 |
| 3,016,895 | 1/1962 | Sein . | |
| 3,832,458 | 8/1974 | Merrill ................................ 424/19 |
| 3,857,932 | 12/1974 | Shepherd et al. . | |
| 3,862,304 | 1/1975 | Kurtz ................................ 424/26 |
| 3,887,699 | 6/1975 | Yolles ................................ 424/19 |
| 3,896,812 | 7/1975 | Kurtz ................................ 128/335.5 |
| 3,896,813 | 7/1975 | Kurtz ................................ 128/335.5 |
| 3,976,071 | 8/1976 | Sadek ................................ 128/335.5 |
| 3,987,797 | 10/1976 | Stephenson ................................ 128/335.5 |
| 3,991,766 | 11/1976 | Schmitt et al. ................................ 128/335.5 |
| 4,148,871 | 4/1979 | Pitt et al. ................................ 424/19 |
| 4,245,635 | 1/1981 | Kontos . | |
| 4,347,234 | 8/1982 | Wahlig et al. ................................ 514/801 |
| 4,371,516 | 2/1983 | Gregory et al. ................................ 424/422 |
| 4,409,332 | 10/1983 | Jefferies et al. ................................ 435/188 |
| 4,419,340 | 12/1983 | Yolles ................................ 424/22 |
| 4,442,051 | 4/1984 | Rowe et al. ................................ 424/37 |
| 4,536,387 | 8/1985 | Sakamoto et al. ................................ 514/774 |

FOREIGN PATENT DOCUMENTS 882541 3/1980 Belgium .
2353285 9/1975 France .
2342741 3/1977 France .
2520229 1/1982 France .
56-122317 9/1981 Japan .
642385 11/1947 United Kingdom .
2091554 1/1982 United Kingdom .

Primary Examiner—Ronald W. Griffin
Attorney, Agent, or Firm—Birch, Stewart, Kolasch & Birch

[57] ABSTRACT

A solid sustained-release preparation in the form of a needle-like or bar-like shape, which consists essentially of an active ingredient and a pharmaceutically acceptable biodegradable carrier (e.g. proteins, preferably collagen, gelatin, and a mixture thereof). The sustained-release preparation can be administered to the body or implanted into the body by injection or an injection-like method and can release the active ingredient at an effective level for a long period of time when administered.

20 Claims, 3 Drawing Sheets

LONG-TERM SUSTAINED-RELEASE PREPARATION

This is a continuation-in-part application of Ser. No. 660,052 filed on Oct. 12, 1984, now abandoned.

The present invention relates to a long-term sustained-release preparation. More particularly, it relates to a long sustained-release preparation in the form of a bar-like or needle-like shaped preparation suitable for injection or injection-like administration, which comprises an active ingredient in admixture with one or more of pharmaceutically acceptable biodegradable carriers which can be implanted into the body. The preparation of the invention is particularly suitable for medicaments which are unstable to heat.

It is known to prepare a medicament embraced within a polymer, for example polyethylene glycol diacrylate polymer, and to implant the product into the body in order to sustain the release of the medicament. However, such a technique has various problems in that the polymer is not biodegradable and hence it must be removed by suitable means after administration and the implanting must be done by an operation with troublesome treatment. Nevertheless, it has been desired to make a sustained-release preparation of many medicaments.

The present inventors have intensively studied on an improved sustained-release preparation or medicaments, and have found that the desired sustained-release preparation can be obtained by admixing an active ingredient with a specific biodegradable carrier and that the formed product of the preparation in the form of a bar-like or needle-like shape is very useful for injection or implanting into the body and can show excellent effect for release-sustaining of the active ingredient.

An object of the present invention is to provide an improved sustained-release preparation. Another object of the invention is to provide a long-term sustained-release preparation in the form of a bar-like or needle-like shaped preparation which can injected or implanted into the body and can release the active ingredient and can maintain the desired level of the active ingredient in blood or in lesional region for a long period of time. A further object of the invention is to provide a method for preparing the sustained-release preparation as set forth above without using any specific binding agent and without heating. A still further object of the invention is to provide a device for administering a sustained-release preparation in the form of a needle-like or bar-like shape. These and other objects and advantages of the present invention will be apparent to persons skilled in the art from the following description.

The sustained-release preparation of the present invention in the form of a bar-like or needle-like shaped preparation consists essentially of (i) an active ingredient in admixture with (ii) one or more of pharmaceutically acceptable biodegradable carriers which can be absorbed or be subject to enzymolysis in body and can be implanted within the body. The sustained-release preparation is formed in a bar-like or needle-like shape and can be injected or implanted into the body.

The active ingredient used in the present invention is not specified, but includes particularly medicaments which are effective in a very small amount and in which their activity is promoted by sustained release, and more particularly medicaments which are unstable to heat. Suitable examples of the active ingredient are tissue plasminogen activator, prostaglandins, prostacyclines, various bio-hormones, interferons, interleukins, tumor necrosis factor, and some other cytokines (e.g. macrophage activating factor, migration inhibitory factor and colony stimulating factor). The term bio-hormones means substances which are produced within the living body and regulate the bio-functions, including growth hormone (GH) such as human growth hormone (HGH), bovine growth hormone (bGH) including biosynthetic product (B-HGH, etc.); growth hormone releasing factors (GRF) which are known as peptides consisting of a number of amino acids of 44, 40, 37 or 29 (e.g. hGRF(1–44)NH$_2$, hGRF(1–29)NH$_2$); somatomedines (SM) such as SM-A, SM-B, SM-C, insulin-like growth factor (IGF)-I, IGF-II, and multiplication stimulating activity (MSA); and calcitonin (i.e. calcium regulating hormone secreted from the mammalian thyroid gland and in non-mammalian species from the ultimobranchial gland).

Interferon, interleukin, tumor necrosis factor, and some other cytokines are somewhat different each other, but are common in that they have very similar molecular weight, are glycoproteins or proteins and have similar pharmacological and physicochemical properties as those of α-interferon as shown in experiments as disclosed hereinafter. All of these compounds are prepared in the desired excellent sustained-release preparation of the present invention.

The above active ingredients may be used alone or in combination of two or more thereof.

The biodegradable carrier used in the present invention means a carrier which can easily be absorbed or be subject to enzymolysis in body and can be implanted into the body. Suitable examples of the biodegradable carrier are proteins such as collagen, gelatin, albumin, or the like. These substances can be used alone or in any combination of two or more thereof, but in view of moldability, collagen or gelatin or a mixture thereof are preferable. Collagen is a protein which is a main protein of connective tissue of animals, has less antigenicity, and hence, has widely been used as a safe operation yarn in various medical operations. The collagen may be an atelocollagen having far less antigenicity which is obtained by removing the telopeptide region by treating collagen with an enzyme (e.g. pepsin) in order to make it safer. Gelatin is a protein derived from collagen. Gelatin is a high molecular weight amphoteric electrolyte which has less antigenicity and the properties of being convertible between sol and gel forms, is inexpensive, and hence it has already been confirmed as a safe substance for medical use.

The medicaments and carriers used in the present invention are preferably purified products, but commercially available products may be used as purchased. The commercially available medicaments and carriers contain usually some appropriate additives such as stabilizers and buffering agents to some extent. For instance, an aqueous collagen solution contains usually a buffer of inorganic or organic salts, such as a phosphate buffer, citrate buffer or acetate buffer. Commercially available interferons contain usually sodium chloride and further human serum albumin, amino acids (e.g. glycine, alanine, etc.), succharides (e.g. glucose, etc.), sugar-alcohols (e.g. mannitol, xylitol, etc.). Other medicaments occasionally contain fetal cow serum, bovine serum albumin, phosphate buffered saline, Tris, etc. These products may be used as obtained, but in view of release-sustaining properties, it is preferable to remove such additives or other components.

The preparation of the present invention contains the active ingredient in an amount in which the active ingredient is usually used. For example, interferon is usually contained in an amount of $10^4$ to $10^9$ IU, preferably $10^5$ to $5 \times 10^8$ IU per dosage unit.

The ratio of the medicament and the carrier is not specified, but for example, interferon is preferably incorporated in an amount of $10^3$ to $10^8$ IU per 1 mg of the carrier.

One of the characteristics of the present invention is in that the preparation can be prepared without using any specific binding agent and further without heat treatment through the steps. The preparation is, therefore, particularly suitable for medicaments which are unstable to heat.

The sustained-release preparation of the present invention can be prepared by the following method.

An active ingredient or an aqueous solution thereof is mixed with a biodegradable carrier or an aqueous solution thereof, and the mixture is homogeneously mixed by stirring while preventing the occurrence of foam as much as possible. By the mixing of the active ingredient and the carrier in the state of a liquid, the active ingredient is incorporated into the carrier matrix. Thereafter, the mixture is dried in order to produce a shaped product having an enough strength for administering to a living body. The drying method is not specified, but it may be dried, for example, by allowing to stand, or by spray-drying or lyophilization. In addition, the mixture may optionally be concentrated at a low temperature before drying, for example, by allowing the solution to stand at room temperature. In the above steps, the mixing step and drying step are usually carried out at room temperature or lower and optionaly under cooling. For instance, the mixing step is usually carried out at about 5° C. to 30° C.; the drying by lyophilization is usually carried out at $-50°$ C. to 0° C.; and the drying by allowing to stand or by spray-drying is usually carried out at room temperature or lower (i.e. about 15° C. to 30° C.). The spray-dry is usually carried out by controlling the temperature of the solution and vessel at room temperature or lower, by which the temperature of the active ingredient can be kept at room temperature or lower and hence no damage is caused to the active ingredient even though it is unstable to heat.

The preparation of the present invention preferably consists substantially of an active ingredient and a biodegradable carrier. That is, when components other than the active ingredient and carrier are present in the preparation of the invention, they occasionally promote the release of active ingredient, and hence, it is preferable not to incorporate such other components as much as possible. However, from the practical viewpoint, the preparation may contain other components originating from the commercially available medicaments and carriers unless they substantially affect the release-sustaining properties. Likewise, the preparation of the invention may pharmaceutically acceptable conventional stabilizers, preservatives, and local anesthetic agents unless they substantially affect the release-sustaining properties.

The preparation thus obtained is optionally pulverized into powders under cooling with dry ice or liquid nitrogen so that the preparation is kept at about $-10°$ C. to about $-100°$ C., or any other conventional pulverization methods at room temperature or lower temperature. The powder is optionally compressed to form some specific shapes, such as a needle-like or fine bar-like shaped preparation (in case of preparation for human, diameter: about 0.5 mm–5 mm, preferably 0.5 mm–1.5 mm, length: about 5 mm–50 mm, preferably, 5 mm–15 mm; in case of preparation for other animals, diameter: about 0.5 mm–10 mm, preferably 0.5 mm–5 mm, length: about 5 mm–100 mm, preferably 5 mm–50 mm), which can be inserted into a body by operation or with a forceps needle for fiberscope, an indwelling needle, or other appropriate administration device as mentioned hereinafter. Alternatively, the powdery preparation is placed into a mold, followed by concentrating at a low temperature, as mentioned hereinbefore, or by lyophilizing to compress and form it into a needle-like or a fine bar-like shaped preparation.

Through all the steps for preparing the desired sustained-release preparations, the procedure is carried out under sterilized conditions because the preparations are to be used as an injection or for implanting into a body.

The long sustained-release preparation of the present invention can be administered to human patients or other animals such as cattle, sheep, pig, rabbit, hen and cock, and the like by operation or by other various methods, for example, by inserting a fine tube into the body at the desired region with an appropriate means, such as catheter, and then inserting the needle-like shaped preparation of the present invention by passing through the inside of the fine tube, or by inserting the preparation of the present invention directly into the body at the lesional region by means of forceps needle of fiberscope.

The present invention provides also an improved device for administering the needle-like or bar-like shaped preparation of the present invention.

The device for administration of the sustained-release preparation and administration manner are explained referring to the accompanying drawings.

The device for administering a needle-like shaped preparation comprises (i) a fine tube and (ii) an inner needle which can freely slide within the fine tube.

Figure 1:
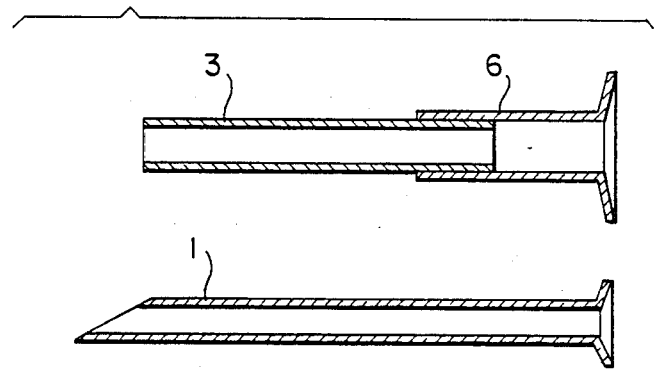
FIG. 1 shows an embodiment of a device for administering the preparation of the present invention which comprises a fine tube and an inner needle.

The fine tube in the above device is a tube having an inner diameter of 0.5 to 10 mm which can be inserted partly into a body. The length of the tube is not specified but may be any size convenient for injection, and is usually in the range of 2 cm to 10 cm. The material for preparing the tube may be any kind of material compatible with the body. The inner needle has a sharp tip as shown in the accompanying FIG. 1 and has an outer diameter as the same as or smaller than the inner diameter of the fine tube.

The device for administering a needle-like shaped preparation is usually held in a holding device (6) in use, but may be used by being held at the tip of forceps needle of fiberscope.

Figure 2:
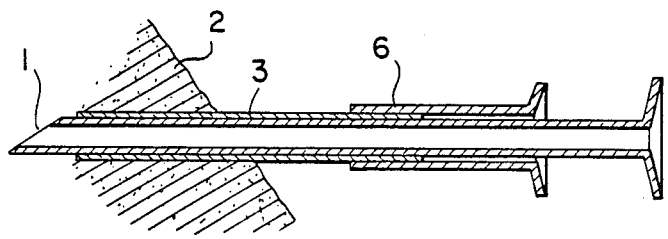
FIG. 2 is an embodiment showing the state that the device as shown in FIG. 1 is stabbed into the body.
Figure 3:
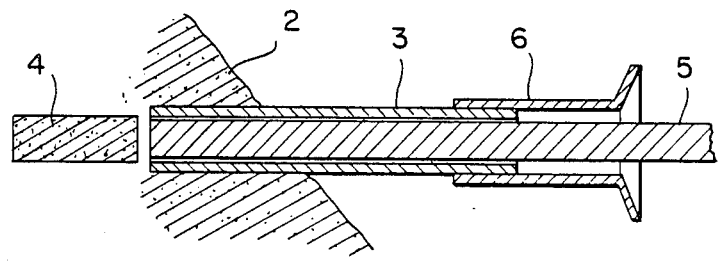
FIG. 3 is an embodiment showing the state that a needle-like shaped solid preparation is administered into the body by the device as shown in FIG. 1.

The administration manner of the needle-like shaped preparation with the above device is explained in more detail below. Firstly, the inner needle (1) is stabbed into a portion of the body (2) and simultaneously the fine tube (3) is inserted into the body by sliding its inner wall along the outer wall of the inner needle (1) (cf. the accompanying FIG. 2). Thereafter, the inner needle (1) is pulled off, and then the needle-like shaped preparation (4) is inserted into the body by passing it through the inner slit of the fine tube (3), and finally the fine tube is removed. The insertion of the needle-like shaped preparation into the body is usually carried out by inserting the preparation into the fine tube after pulling off of the inner needle (1), pushing the preparation with a pushing pole (5) into the inside of the body (2) (cf. the accompanying FIG. 3). The pushing pole (5) may be any pole which can be inserted into and can freely slide inside the fine tube (3), and the above inner needle (1) may also be used as the pushing pole.

In order to insert the preparation of the present invention into a deep region of the body, i.e. internal organs such as the stomach wall, the device for a fiberscope may be used. Easy handling for a fiberscope can effect procedures such as stabbing of an inner needle, insertion of the fine tube, pulling off of the inner needle, administration of the preparation and taking off of the fine tube.

The preparation which can be administered by the above device may be any needle-like or bar-like shaped preparation which can be inserted and held within the fine tube (3).

An alternative device for insertion of a needle-like shaped solid preparation is an injection needle provided with a inner pushing pole which can smoothly slide within the slit of the needle. The injection needle includes the conventional injection needle, and the pushing pole has an outer diameter which is equal to or smaller than the inner diameter of the injection needle and can push the needle-like shaped solid preparation having a diameter of 0.5 to 10 mm.

The device for insertion of a needle-like shaped solid preparation may be held with conventional holding device (7), but may be used by holding it at the tip of a forceps needle for a fiberscope.

The administration of the needle-like shaped solid preparation of the present invention is explained in more detail below.

Figure 4:
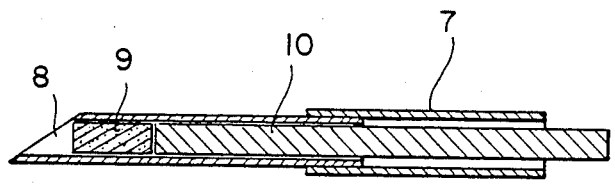
FIG. 4 shows an embodiment of a needle for administering a needle-like shaped solid preparation of the present invention wherein the solid preparation is held.
Figure 5:
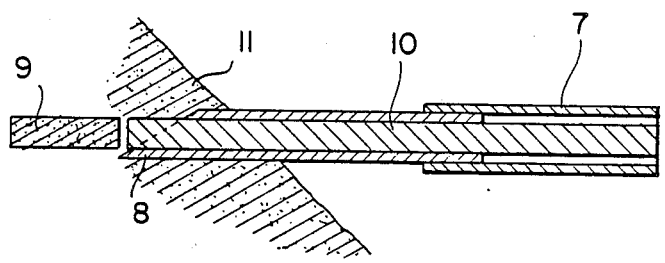
FIG. 5 is an embodiment showing the state that the needle-like shaped solid preparation is administered into the body with the administration needle as shown in FIG. 4.
Figure 6:
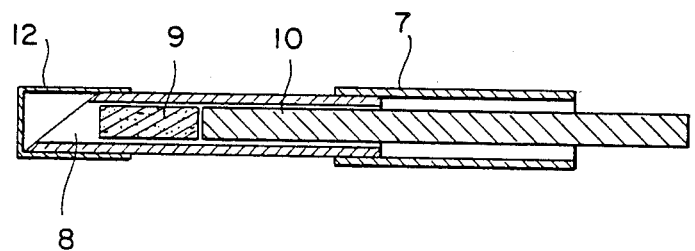
FIG. 6 is an embodiment of a needle for administering a needle-like shaped solid preparation of the present invention which is provided with a removable cover for preventing the held solid preparation from falling down.

Initially, the needle-like shaped solid preparation (9) is held within the injection needle (8) (cf. the accompanying FIG. 4), the injection needle (8) is stabbed into the portion of the body (11) and simultaneously the preparation is administered into the body (11) by pushing it with a pushing pole (10) (cf. the accompanying FIG. 5). In order to administer the preparation to a deep region of the body such as the stomach wall, it may be administered with a fiberscope as mentioned above. In such a case, to prevent the preparation from falling out of the needle, it is preferable to provide a removable cover (12) at the tip of the needle (cf. the accompanying FIG. 6). The solid preparation useful for the above administration may be in any form such as needle-like or bar-like shape which can be held in a conventional injection needle.

As explained above, according to the device for injection of the present invention, the preparation of the present invention can easily be administered, for example, into internal organs with a fiberscope, and systematically or topically at the body surface by operation or with a device or needle as mentioned above. These methods are practically and clinically very useful, and it is a novel idea that a biodegradable solid preparation is administered in the above-mentioned manner.

The present invention is illustrated by the following Experiments and Examples, but should not be construed to be limited thereto.

EXPERIMENT 1

There were used as the test samples a needle-shaped preparation of α-interferon-collagen prepared in Example 1 disclosed hereinafter (Sample A) and a reference (an aqueous injection of α-interferon originated from Namalwa cells). The test samples were each administered intramuscularly to rabbit, and the change of level in blood of the active ingredient with lapse of time was measured by RIA (radioimmunoassay) method. Two rabbits were used for each sample, and the test samples were each administered in a dose of $10^6$ U/kg. The blood level is shown as an average in two rabbits.

Figure 7:
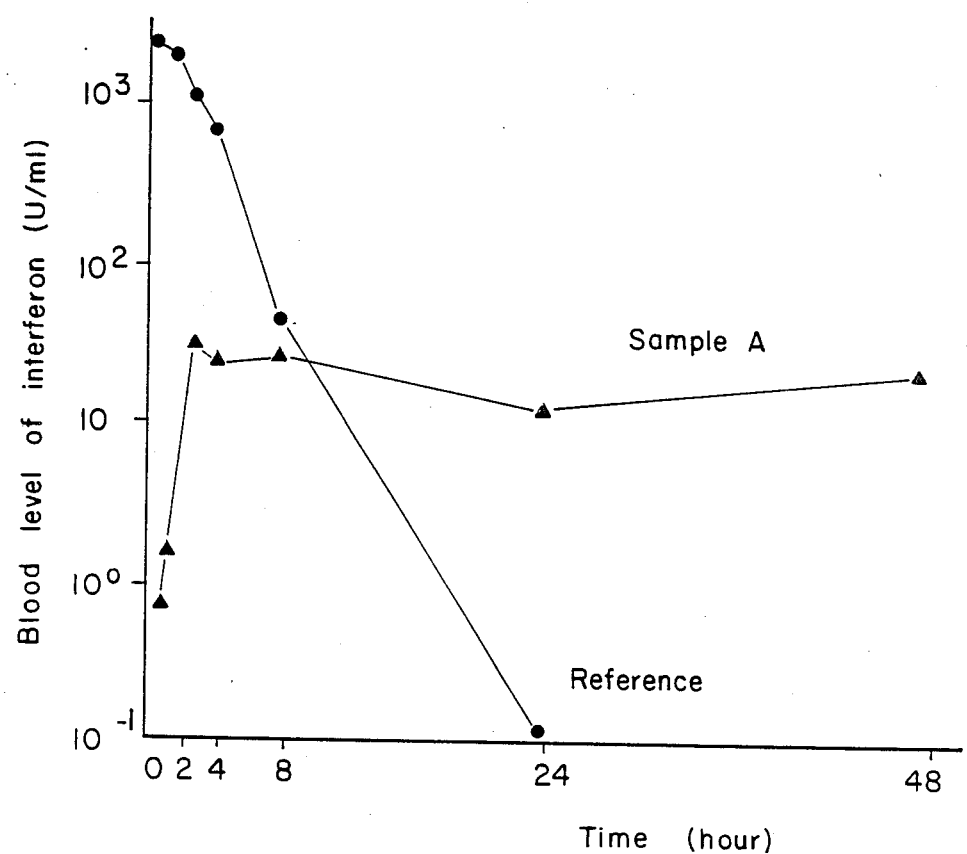
FIG. 7 is a graph showing the relation of the blood level of an active ingredient and time elapsed after intramuscular administration of the preparation in rabbits.

The results are shown in the accompanying FIG. 7. In FIG. 7, ▮ is the graph of Sample A, and ● is that of reference (α-interferon aqueous injection). As is clear from the figure, the Sample A showed release-sustaining properties, and even after 48 hours, the blood level of several tens unit/ml was maintained.

Thus, it is suggested by in vivo tests using rabbits that the preparation of the present invention is useful clinically.

EXAMPLE 1

An aqueous solution of α-interferon (titer: 4.9 MU/ml) (100 ml) and 2% atelocollagen (50 g) are homogeneously mixed with stirring while preventing occurrence of foam as much as possible. The mixture is lyophilized and pulverized at a low temperature using liquid nitrogen. The pulverized product thus obtained is formed under compression to give a needle-shaped sustained-release preparation (A) wherein interferon is contained in an amount of 10 MU per 1 needle.

EXAMPLE 2

A commercially available aqueous solution of α-interferon (α-interferon titer 4.9 MU/ml, human serum albumin 1.5 mg/ml) (100 ml) and 2% atelocollagen (50 g) are homogeneously mixed while preventing occurrence of foam as much as possible. The mixture is lyophilized and pulverized at a low temperature using liquid nitrogen. The pulverized product thus obtained is subjected to compression molding to give a needle-like shaped sustained-release preparation (Sample B) wherein interferon is contained in an amount of 10 MU per 1 needle.

EXAMPLE 3

An aqueous solution of α-interferon (titer, 4.9 MU/ml) (100 ml) and 2% collagen (50 g) are homogeneously mixed while preventing occurrence of foam as much as possible. The mixture is lyophilized and pulverized at a low temperature using liquid nitrogen. The pulverized product thus obtained is subjected to a compression molding to give a bar-like shaped sustained-release preparation (Sample C) wherein interferon is contained in an amount of 5 MU per 1 bar.

EXAMPLE 4

An aqueous solution of α-interferon (titer, 4.9 MU/ml) (100 ml) and atelocollagen powder (1 g) are mixed and the mixture is dissolved by adding thereto 0.1 N hydrochloric acid, and the resulting solution is entered into a mold and lyophilized. The lyophilized product is formed under compression to give a needle-shaped sustained-release preparation (Sample D) wherein interferon is contained in an amount of 10 MU per 1 needle.

EXAMPLE 5

B-HGH (biosynthetic human growth hormone containing glycine 800 mg) (100 IU) is dissolved in 10 % aqueous gelatin solution (3 ml). The mixture is lyophilized and pulverized at a low temperature using liquid nitrogen. The pulverized product is compressed in a mold to give a needle-like shaped, sustained-release preparation.

EXAMPLE 6 hGRF(1-29)NH$_2$ (i.e. human growth hormone-releasing factor) (1 mg) is dissolved in 2 % aqueous atelocollagen solution (2 ml). The mixture is lyophilized and pulverized at a low temperature using liquid nitrogen. The pulverized product is compressed in a mold to give a bar-like shaped, sustained-release preparation.

EXAMPLE 7

Gelatin (10 g) is dissolved in distilled water (100 ml). To the solution (5 ml) is added IGF-1 (insulin-like growth factor-1) (20 mg), and the mixture is lyophilized and pulverized at a low temperature using liquid nitrogen to obtain a powder. The powdery product is compressed in a mold to give a needle-like shaped, sustained-release preparation.

EXAMPLE 8

Collagen (10 g) is dissolved in an aqueous solution (100 ml) containing $1 \times 10^5$ U of human GM-CSF (granulocyte-macrophage-colony stimulating factor), and the solution is lyophilized and pulverized at a low temperature using liquid nitrogen. The pulverized product is compressed in a mold to give a bar-like shaped sustained-release preparation.

What is claimed is:

1. A method for the preparation of a solid sustained-release preparation, which comprises mixing under aqueous conditions a physiologically active ingredient that is unstable to heat and a pharmaceutically acceptable biodegradable protein carrier to incorporate the active ingredient in a carrier matrix to a degree sufficient to provide sustained-release properties; drying the resulting mixture; and then forming the dried material into the form of a needle-like or bar-like shape.

2. The method according to claim 1, wherein said biodegradable carrier is collagen, atelocollagen or gelatin.

3. The method according to claim 2, wherein said biodegradable carrier is collagen.

4. The method according to claim 1, wherein said active ingredient is a member selected from the group consisting of tissue plasminogen activator, prostaglandins, prostacyclines, bio-hormones, interferons, interleukins, tumor necrosis factor and other cytokines.

5. The method according to claim 1, wherein said active ingredient is a member selected from the group consisting of interferons, interleukins, tumor necrosis factor, growth hormone, growth hormone releasing factor, somatomedines, calcitonin, macrophage activating factor, migration inhibitory factor, and colony stimulating factor.

6. The method according to claim 1, wherein said mixing is conducted at a temperature of from 5° to 30° C.

7. The method according to claim 1, wherein said drying is conducted at a temperature of from 15° to 30° C.

8. The method according to claim 6, wherein said drying is conducted at a temperature of from 15° to 30° C.

9. The method according to claim 1, wherein said drying is performed by lyophilization at a temperature of from −50° C. to 0° C.

10. The method according to claim 9, wherein the product obtained from said lyophilization is subjected to pulverization at a temperature of from −100° C. to about room temperature.

11. The method according to claim 4, wherein said biodegradable carrier is collagen.

12. The method according to claim 5, wherein said biodegradable carrier is collagen.

13. The method according to claim 6, wherein said biodegradable carrier is collagen.

14. The method according to claim 7, wherein said biodegradable carrier is collagen.

15. The method according to claim 8, wherein said biodegradable carrier is collagen.

16. The method according to claim 1, wherein said sustained-release preparation is prepared without the use of any binding agent.

17. The method according to claim 3, wherein said sustained-release preparation is prepared without the use of any binding agent.

18. The method according to claim 8, wherein said sustained-release preparation is prepared without the use of any binding agent.

19. The method according to claim 10, wherein said sustained-release preparation is prepared without the use of any binding agent.

20. The method according to claim 14, wherein said sustained-release preparation is prepared without the use of any binding agent.

* * * * *